United States Patent [19]

Gard

[11] Patent Number: 4,853,616
[45] Date of Patent: * Aug. 1, 1989

[54] DETECTION OF WATER SATURATION IN INSULATION AT CASED ROAD CROSSINGS

[75] Inventor: Michael F. Gard, Plano, Tex.

[73] Assignee: Atlantic Richfield Company, Los Angeles, Calif.

[*] Notice: The portion of the term of this patent subsequent to Aug. 1, 2006 has been disclaimed.

[21] Appl. No.: 222,453

[22] Filed: Jul. 21, 1988

[51] Int. Cl.[4] ............................................. G01R 27/14
[52] U.S. Cl. .................................. 324/65 R; 324/525; 324/551; 340/604
[58] Field of Search .................... 324/65 R, 541, 539, 324/525, 544, 551; 340/603, 604, 605; 174/11 R; 73/40.5 R

[56] References Cited

U.S. PATENT DOCUMENTS

| | | | |
|---|---|---|---|
| 3,803,485 | 4/1974 | Crites et al. | 324/65 R |
| 4,029,889 | 6/1977 | Mizuochi | 174/11 R |
| 4,506,540 | 3/1985 | Marsh | 340/604 |

Primary Examiner—Reinhard J. Eisenzopf
Assistant Examiner—Anthony L. Miele
Attorney, Agent, or Firm—Albert C. Metrailer

[57] ABSTRACT

A method for detecting water saturation of thermal insulation located between a flowline and metal sheathing at a location where the flowline is positioned in a metal casing. Electrical resistance measurements are made between the metal sheathing and flowline, between the casing and the sheathing, and between the casing and the flowline. The resistance values and/or direct voltage and current measurements are used to determine actual resistance through the insulation as an indication of water saturation.

8 Claims, 1 Drawing Sheet

4,853,616

DETECTION OF WATER SATURATION IN INSULATION AT CASED ROAD CROSSINGS

BACKGROUND OF THE INVENTION

The present invention relates to external corrosion of insulated flowlines or pipelines caused by water saturation of the insulation and more particularly to the use of electrical resistance measurements to detect the presence of water in the thermal insulation at road crossings and other locations where the pipeline is inaccessible because it is protected by an external metal casing.

In areas with cold climates, it is often necessary to provide thermal insulation around oil and gas flowlines, or pipelines, to either prevent the oil products from becoming too viscous by chilling or to protect permafrost from thawing. The thermal insulation is normally held in place and mechanically protected by a thin metal sheathing. If the thermal insulation becomes water saturated, corrosion of the external flowline surface will result. Where the insulated flowline is physically accessible, infrared and/or neutron backscatter inspection techniques are commonly used to detect such water saturation without having to disassemble the insulation jacket.

In certain areas, such as road crossings, the insulated flowline must be buried. In such areas the flowline is mechanically protected by an additional heavy steel casing. One or more of such insulated pipelines are typically positioned within such casing by insulating support members which may be called stand-offs or spiders. In these areas, the flowline is not accessible and the usual water detection techniques cannot be used. Since the replacement costs of such a road crossing is high, on the order of $250,000, and requires more down time than an exposed flowline section, it is very important to detect the presence of water in the flowline insulation so that corrective steps can be planned before corrosion becomes dangerous.

SUMMARY OF THE INVENTION

I have found that the electrical resistance of thermal insulation is inversely related to the level of water saturation and that therefore a measurement of electrical resistance between a flowline and protective metal sheathing can indicate a level of water saturation of the thermal insulation and in turn indicate the presence or absence of external flowline corrosion. I have also found that there are other possible electrical paths from the sheathing to the flowline so that if a low resistance measurement is obtained, additional resistance measurements between the sheathing and casing and the casing and flowline should be made to verify the presence of water in the thermal insulation.

A first embodiment of the method of the present invention includes the steps of paring back or removing portions of the metal sheathing at the ends of a cased insulated flowline section to electrically isolate the sheathing section within the casing and then (1) measuring electrical resistance between the sheathing section within the casing and the flowline, (2) measuring electrical resistance between the casing and the sheathing section within the casing, and (3) measuring electrical resistance between the casing and the flowline. The presence or absence of water saturation in the thermal insulation is then determined from the measured resistance values.

In an alternate embodiment, after isolation of the sheathing section within the casing, a voltage source is applied between the casing and flowline and measurements are taken of the voltage source current and the voltage between the sheathing and the flowline. Then the voltage source is applied between the flowline and the sheathing section within the casing and measurements are taken of the voltage source voltage, the voltage source current, and the voltage between the casing and flowline. The measured voltage and current values are then used to calculate the resistance of the insulation between sheathing and flowline and to infer therefrom the level of water saturation. If desired, the measured values can also be used to calculate the resistances between the casing and flowline and between the casing and sheathing section within the casing.

A third embodiment involves a modification of the second embodiment in which an ohmmeter is used to measure apparent resistances between the casing and flowline and between the sheathing section within the casing and flowline instead of measuring the voltage source currents at each location. The apparent resistances and measured voltages are then used to calculate the sheathing to flowline resistance and to infer the level of water saturation. As in the second embodiment, the resistances between casing and flowline and casing and sheathing section within the casing may also be calculated from the measured values.

DESCRIPTION OF THE DRAWINGS

The present invention may be better understood by reading the following detailed description of the preferred embodiments with reference to the accompanying drawings wherein.

DESCRIPTION OF THE PREFERRED EMBODIMENTS

Figure 1:
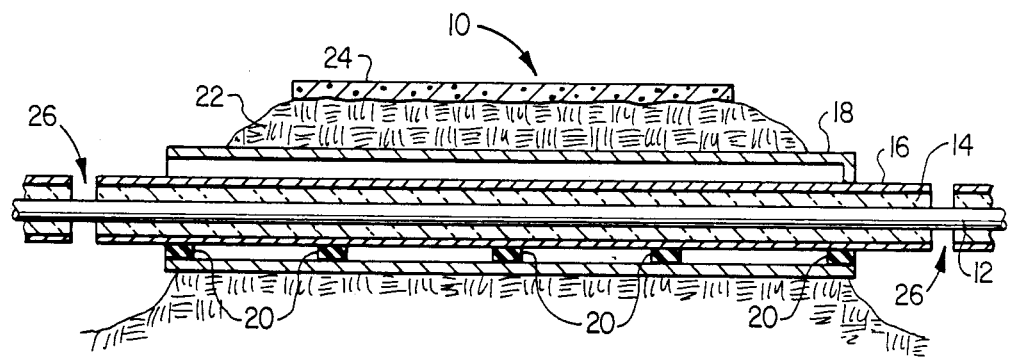
FIG. 1 is a cross sectional illustration of an insulated flowline road crossing structure.

With reference now to FIG. 1, there is illustrated a typical insulated flowline road crossing 10. A flowline 12 is surrounded by thermal insulation 14. The insulation 14 is surrounded by thin metal sheathing 16. The insulated flowline is positioned within a casing 18. A number of electrical insulating stand-offs or spiders 20 are used to position the insulated flowline assembly within casing 18 while avoiding any electrical contact between the sheathing 16 and the casing 18. The casing 18 is typically buried in the roadway 10 foundation material 22 usually formed of earth or gravel. The roadway may include a paved surface 24. In the areas 26, the metal sheathing 16 and insulation 14 have been pared back or removed to electrically isolate the section of sheathing 16 which lies within casing 18 and to allow electrical contact to flowline 12 at this crossing.

While a single insulated flowline assembly has been illustrated within casing 18, a typical road crossing may include a plurality of such flowline assemblies.

From the FIG. 1 illustration of a typical flowline road crossing, it can be seen that normal techniques for detecting water saturation through the sheathing 16 cannot be used since the flowline section within the casing 18 is not accessible. It would also appear that a simple ohmmeter could be used to measure resistance between the sheathing section 16 within casing 18 and the flowline 12 to determine water saturation. Laboratory tests indicate that dry insulation has an electrical resistivity in the megohm range while thoroughly saturated insulation may have an electrical resistivity as low as a few hundred ohms. Thus water saturation should easily be indicated by a low resistance measurement. However, we have found that a low resistance measurement between the sheathing 16 and flowline 12 can be caused by other sources. As illustrated in FIG. 1, the casing 18 is in direct contact with the earth 22. At some other location, possibly distant from the road crossing 10, flowline 12 will, in essentially all cases, also be in contact with the earth. If the insulating stand-offs 20 are in good condition, the circuit between flowline 12 and casing 18 through the earth should have no effect on the measurement between sheathing 16 and flowline 12. However, if insulators 20 are defective or for any other reason a conductive path between sheathing 16 and casing 18 has been created, the apparent resistance measured from sheathing 16 to flowline 12 will be lower than the actual resistance of the insulation 14.

In view of the possible errors in taking a single resistance measurement, the first embodiment of the present invention involves taking two additional resistance measurements to verify a straightforward measurement of resistance between sheathing 16 and flowline 12. The first step of the method is to remove a portion of the sheathing 16 and insulation 14 at the locations 26 illustrated in FIG. 1. A resistance measurement is then made between sheathing 16 and flowline 12. Then electrical resistance is measured between the casing 18 and the sheathing section 16 within the casing. Finally, electrical resistance is measured between the casing 18 and flowline 12. The first step in determining whether the insulation 14 is water saturated is to simply compare the resistance measured between flowline 12 and sheathing 16 against known resistance values for dry and saturated insulation in similar installations. For example, if the measured resistance is in the range of 0.1 to 1.0 megohm or above, it can be assumed that the insulation 14 is essentially dry. If the measured resistance is lower, the insulation may be water saturated to some extent. However, the other measured resistances must also be considered before concluding that the low resistance value is a result of water saturation of insulation 14. In general, if either of the other two measured resistances is low, that is on the order of the low resistance measured between sheathing 16 and flowline 12, there will be some uncertainty as to the presence of water in insulation 14. For example, even if the stand-offs 20 are in good condition and provide near perfect electrical insulation, a measurement of resistance between sheathing 16 and casing 18 may indicate low resistance if the insulation 14 is water saturated and the resistance of ground 22 is relatively low.

The resistance measurements discussed above may be made in several ways. The most straightforward is to use a standard ohmmeter which directly indicates resistance of the measurement path. Alternatively, a voltage may be applied to the circuit being measured, for example, by use of the battery, and voltage and current meters may be used to measure the applied voltage and the current flowing from the voltage source. Resistance is then determined by dividing the measured voltage by the measured current. Since the metal to fluid current paths will typically exhibit some polarization effects, it may be preferred to use a high voltage source or an AC voltage source in making the resistance measurements. Since typical ohmmeters use a low voltage DC source, they are more likely to give an erroneous reading in this situation.

Figure 2:
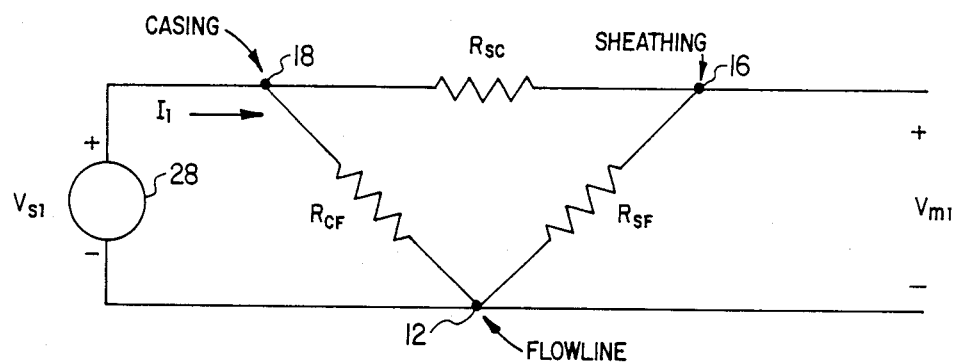
FIGS. 2 and 3 are electrical schematic illustrations of equivalent resistances found in the FIG. 1 structure and also illustrate application of a voltage source as used in the second and third embodiments.
Figure 3:
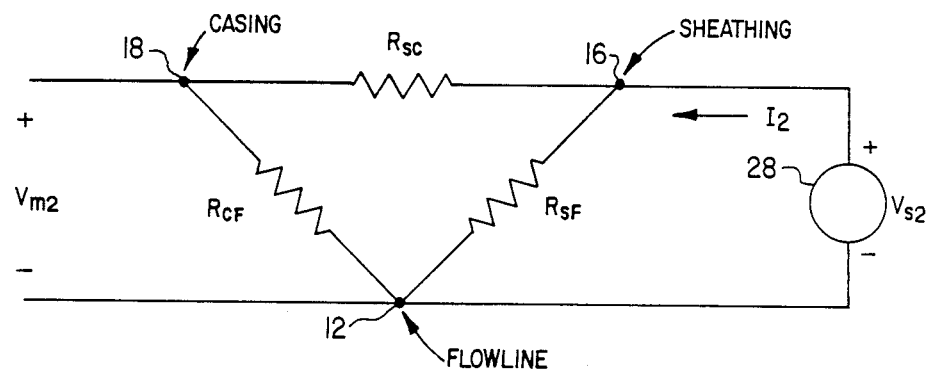

With reference now to FIGS. 2 and 3, there is provided an illustration of the resistive network formed by the flowline crossing 10 of FIG. 1 and a method by which the actual values of each of the three resistances may be determined to overcome ambiguity in the above-described first embodiment. In FIGS. 2 and 3, there are illustrated three resistors $R_{SC}$, $R_{SF}$, and $R_{CF}$ connected in a delta configuration. Resistor $R_{SC}$ represents the resistance between the sheathing 16 and casing 18. $R_{SF}$ represents the resistance between the sheathing 16 and flowline 12. $R_{CF}$ represents the resistance between the casing 18 and flowline 12. The nodes, or connection points, between the resistors each represent one of the three metal elements of FIG. 1, that is the flowline 12, the sheathing 16, and the casing 18. The resistance $R_{SF}$ is the resistance of the insulation 14 which needs to be measured in order to infer the water saturation level of insulation 14. However, as illustrated, the series connection of resistors $R_{SC}$ and $R_{CF}$ is connected in parallel with $R_{SF}$ so that it cannot be directly measured. As is apparent, it is not physically possible to separate any of the resistances from the loop which would otherwise allow separate measurement of each of the resistances. Instead, all measurements must be taken at the nodes 12, 16 and 18.

With reference to FIGS. 2 and 3, a second embodiment of the invention will be described. In a first step of the method as illustrated in FIG. 2, a voltage source 28 is connected between flowline 12 and casing 18. Tee actual voltage of the source 28, $V_{s1}$, and the current flowing from the source, $I_1$, are then measured. In addition, the voltage, $V_{M1}$, between sheathing 16 and flowline 12 is also measured.

The voltage source 28 is then moved, as illustrated in FIG. 3, and connected between the sheathing 16 and flowline 12. Measurements are then taken of the actual voltage, $V_{s2}$, of source 28 and the output current $I_2$. In addition, voltage between flowline 12 and casing 18, $V_{M2}$, is also measured.

The voltages and currents thus measured are sufficient to calculate the actual values of each of the resistances $R_{SC}$, $R_{SF}$ and $R_{CF}$. One way of calculating the resistances is as follows. First, two correction values designated $B_1$ and $B_2$ are calculated according to the following formulas:

$$B_1 = V_{m1}/(V_{s1} - V_{m1})$$

$$B_2 = V_{m2}/(V_{s2} - V_{m2})$$

Then the actual resistance of $R_{SF}$ can be calculated as follows:

$$R_{SF} = (V_{s2}/I_2)(1 + B_1 + B_2)/(1 + B_2).$$

The value of $R_{SF}$ thus calculated will be the actual value of the thermal insulation 14 electrical resistance and thus will indicate the presence of water saturation from which the rate of external flowline corrosion can be inferred. For these purposes, it is not necessary to calculate the resistances $R_{CF}$ and $R_{SF}$. However, in order to verify the accuracy of the measurements and result and, for example, to determine whether insulators 20 are in good condition, the other resistances may be calculated as follows:

$$R_{CF}=(V_{s1}/I_1)(1+B_1+B_2)/(1+B_1).$$

$$R_{SC}=(V_{s1}/I_1)(1+1+B_2)/(B_2(1+B_1)).$$

It will be appreciated that the ratios $V_{s2}/I_2$ and $V_{s1}/I_1$ correspond to apparent resistance values which could be measured by use of an ohmmeter as described above with respect to the first embodiment. In practice, we have found that use of such apparent resistances, that is those measured by a direct measurement using an ohmmeter, are quite suitable for use in calculating the values of $R_{SF}$, $R_{CF}$ and $R_{SC}$ as discussed above. When such direct resistance measurements are made, it is not necessary to measure the currents $I_1$ and $I_2$ as illustrated in FIGS. 2 and 3. Therefore, the field equipment can include merely a voltage source, a voltmeter and an ohmmeter for making measurements necessary to calculate the desired actual resistances.

While the present invention has been illustrated and described with respect to use of certain apparatus and particular steps, it is apparent that various modifications and changes can be made therein within the scope of the present invention as defined by the appended claims.

What is claimed is:

1. A method for detecting water saturation of thermal insulation positioned between a flowline and metal sheathing at a location where said flowline is positioned in a metal casing by electrical insulating stand-offs, both said flowline and casing being in contact with the earth, comprising:

removing portions of said sheathing near each end of said casing to electrically isolate that section of the sheathing positioned within the casing, connecting a voltage source between the casing and flowline, measuring the voltage, $V_{s1}$, of the voltage source, measuring the current, $I_1$, flowing from the voltage source and measuring the voltage, $V_{m1}$, between the sheathing section within the casing and the flowline, connecting the voltage source between the sheathing section within the casing and the flowline, measuring the voltage, $V_{s2}$, of the voltage source, measuring the current, $I_2$, flowing from the voltage source, and measuring the voltage, $V_{m2}$, between the casing and the flowline, and using the measured values, calculating the electrical resistance of the thermal insulation between the flowline and the sheathing section within the casing.

2. The method of claim 1 wherein the electrical resistance, $R_{SF}$, of the thermal insulation between the flowline and the sheathing section within the casing is calculated by:

calculating correction terms $B_1$ and $B_2$ according to the formulas;

$$B_1=V_{m1}/(V_{s1}-V_{m1})$$

$$B_2=V_{m2}/(V_{s2}-V_{m2});$$

and calculating $R_{SF}$ according to the formula;

$$R_{SF}=(V_{s2}/I_2)(1+B_1+B_2)/(1+B_2).$$

3. The method of claim 2 further including the step of calculating the resistance, $R_{CF}$, between the casing and the flowline according to the formula:

$$R_{CF}=(V_{s1}/I_1)(1+B_1+B_2)/(1+B_1).$$

4. The method of claim 2 further including the step of calculating the resistance, $R_{SC}$, between the casing and the sheathing section within the casing according to the formula:

$$R_{SC}=(V_{s1}/I_1)(1+B_1+B_2)/(B_2(1+B_1)).$$

5. A method for detecting water saturation of thermal insulation positioned between a flowline and metal sheathing at a location where said flowline is positioned in a metal casing by electrical insulating stand-offs, both said flowline and casing being in contact with the earth, comprising:

removing portions of said sheathing near each end of said casing to electrically isolate that section of the sheathing positioned within the casing, connecting a voltage source between the casing and flowline, measuring the voltage, $V_{s1}$, of the voltage source, and measuring the voltage, $V_{m1}$, between the sheathing section within the casing and the flowline, connecting the voltage source between the sheathing section within the casing and the flowline, measuring the voltage, $V_{s2}$, of the voltage source, and measuring the voltage, $V_{m2}$, between the casing and the flowline, using an ohmmeter to measure the apparent resistance, $R_1$, between the casing and flowline and the apparent resistance, $R_2$, between the flowline and the sheathing section within the casing, and using the measured values, calculating the electrical resistance of the thermal insulation between the flowline and the sheathing section within the casing.

6. The method of claim 5 wherein the electrical resistance, $R_{SF}$, of the thermal insulation between the flowline and the sheathing section within the casing is calculated by:

calculating correction terms $B_1$ and $B_2$ according to the formulas;

$$B_1=V_{m1}/(V_{s1}-V_{m1})$$

$$B_2=V_{m2}/(V_{s2}-V_{m2});$$

and calculating $R_{SF}$ according to the formula;

$$R_{SF}=R_2(1+B_1+B_2)/(1+B_2).$$

7. The method of claim 6 further including the step of calculating the resistance, $R_{CF}$, between the casing and the flowline according to the formula:

$$R_{CF}=R_1(1+B_1+B_2)/(1+B_1).$$

8. The method of claim 6 further including the step of calculating the resistance, $R_{SC}$, between the casing and the sheathing section within the casing according to the formula:

$$R_{SC}=R_1(1+B_1+B_2)/(B_2(1+B_1)).$$

* * * * *